(12) United States Patent
Han

(10) Patent No.: US 12,740,893 B2
(45) Date of Patent: Sep. 22, 2026

(54) EYE DISEASE IMPLANT DEVICE HAVING FORMATION PRESSURE IN ANTERIOR CHAMBER ADJUSTED

(71) Applicant: MICROT INC., Seoul (KR)

(72) Inventor: Jong Chul Han, Seoul (KR)

(73) Assignee: MICROT INC., Seoul (KR)

( * ) Notice: Subject to any disclaimer, the term of this patent is extended or adjusted under 35 U.S.C. 154(b) by 329 days.

(21) Appl. No.: 18/008,314

(22) PCT Filed: Dec. 15, 2020

(86) PCT No.: PCT/KR2020/018322
§ 371 (c)(1),
(2) Date: Dec. 5, 2022

(87) PCT Pub. No.: WO2022/114358
PCT Pub. Date: Jun. 2, 2022

(65) Prior Publication Data

US 2025/0099296 A1 Mar. 27, 2025

(30) Foreign Application Priority Data

Nov. 30, 2020 (KR) ........................ 10-2020-0164025

(51) Int. Cl.
*A61F 9/007* (2006.01)

(52) U.S. Cl.
CPC ................................ *A61F 9/00781* (2013.01)

(58) Field of Classification Search
CPC .................................................. A61F 9/00781
See application file for complete search history.

(56) References Cited

U.S. PATENT DOCUMENTS 9,561,133 B2 2/2017 Torello et al.
2010/0241046 A1* 9/2010 Pinchuk ................ A61L 31/146 604/8

(Continued)

FOREIGN PATENT DOCUMENTS

JP 2016532458 A 10/2016
JP 2017526504 A 9/2017

(Continued)

OTHER PUBLICATIONS

PCT International Search Report from PCT/KR2020/018322, mailed Aug. 26, 2021, 7 pages.

*Primary Examiner* — Ariana Zimbouski
(74) *Attorney, Agent, or Firm* — ZION IP; Byungwoong Park

(57) ABSTRACT

An eye disease implant device for adjusting intraocular pressure may comprise: a tube body, one end of which is inserted into the anterior chamber of an eyeball and the other end of which is inserted into the conjunctival tissue or tenon tissue of the eyeball, the tube body including a hollow channel and being configured to discharge aqueous humor, produced in the anterior chamber of the eyeball, to the conjunctival tissue or tenon tissue via the hollow channel; and a wick which is configured to be inserted into the hollow channel of the tube body in order to adjust the formation pressure in the anterior chamber through the tube body. In the eye disease implant device, each part, such as the inner diameter of the tube and the diameter of the wick inserted into the tube, is designed such that the optimal formation pressure in the anterior chamber of the eyeball is achieved when lowering the intraocular pressure through the tube inserted into the anterior chamber. Thus, the present invention has the advantage of being able to solve problems such as insufficient discharge of aqueous humor or low intraocu- (Continued)

lar pressure caused by excessive discharge of aqueous humor.

10 Claims, 7 Drawing Sheets

(56) References Cited

U.S. PATENT DOCUMENTS

| | | | | |
|---|---|---|---|---|
| 2010/0249691 | A1* | 9/2010 | Van Der Mooren | A61F 9/00781 604/9 |
| 2015/0320357 | A1* | 11/2015 | Kuraguntla | A61B 5/6862 600/300 |
| 2016/0302967 | A1* | 10/2016 | Ahn | A61M 27/006 |
| 2017/0020730 | A1* | 1/2017 | Chew | A61F 9/00781 |
| 2018/0078417 | A1* | 3/2018 | Ahmed | A61F 9/00781 |
| 2018/0325733 | A1 | 11/2018 | Camras et al. | |
| 2019/0062951 | A1* | 2/2019 | Rizk | B29C 55/005 |

FOREIGN PATENT DOCUMENTS

| | | | |
|---|---|---|---|
| KR | 2020000021075 | U | 12/2000 |
| KR | 1020120064679 | A | 6/2012 |
| KR | 1020150034010 | A | 4/2015 |
| KR | 1020200026150 | A | 3/2020 |
| WO | 2011020633 | A1 | 2/2011 |
| WO | 2016033270 | A1 | 3/2016 |

* cited by examiner

EYE DISEASE IMPLANT DEVICE HAVING FORMATION PRESSURE IN ANTERIOR CHAMBER ADJUSTED

CROSS-REFERENCE TO RELATED APPLICATIONS

This application is a national phase entry pursuant to 35 U.S.C. § 371 of International Application No. PCT/KR2020/018322, filed Dec. 15, 2020, which claims priority to Korean Application No. 10-2020-0164025, filed Nov. 30, 2020, the entire contents of each of which are incorporated by reference herein for all purposes.

TECHNICAL FIELD

Examples relate to an eye disease implant device and, more particularly, to an eye disease implant device in which the optimal formation pressure in an anterior chamber of an eye is achieved by an appropriate combination of a tube and a wick inserted into the tube when lowering intraocular pressure by discharging aqueous humor through the tube inserted into the eye, and the tube and an implant body are able to be coupled to or decoupled from each other according to need or circumstances.

BACKGROUND ART

In case of a glaucoma patient whose intraocular pressure is not controlled even when the intraocular pressure depressor is used, the intraocular pressure is lowered by making a bypass so that the aqueous humor is discharged under the conjunctiva outside the eye from the anterior chamber of the eye. In the glaucoma filtration procedure that makes a bypass or fistula for discharging the aqueous humor, trabeculectomy may often fail to control intraocular pressure because of reduced discharge of the aqueous humor due to re-blockage of the bypass after the surgery. If the primary surgery is not successive and the glaucoma filtration procedure needs to be performed again, the frequency of the blockage of the bypass after the surgery is increased, and the success rate of surgery is not good.

In addition, depending on the type of glaucoma, a so-called intractable glaucoma, such as neovascular glaucoma or secondary glaucoma caused by uveitis, also has a bad surgical result after the trabeculectomy due to frequent blockage of the bypass. In the case of the eye having a failed glaucoma filtration history or intractable glaucoma, a glaucoma implant surgery is performed to prevent the blockage of the bypass to increase the success rate of the surgery. Up to now, the glaucoma implant surgery has been used as an alternative to the trabeculectomy especially in various kinds of glaucoma, which is difficult to treat, in that the glaucoma implant surgery not only effectively reduces intraocular pressure, but also shows the predictable clinical results after the surgery according to the fixed inner diameter of the tube.

However, an existing glaucoma implant used in the glaucoma implant surgery can cause various problems such as difficulty of surgery, postoperative exposure and infection, eye exercise disorders and their attendant diplopia, or the like, due to the relative large size of the implant, and complications caused therefrom. Therefore, recently, micro-invasive glaucoma surgery (MIGS) using a small size glaucoma implant tool has been developed so that intraocular pressure is lowered and the side effects after a surgery due to the large size of the implant tool are reduced as well by using the glaucoma implant relatively easily.

Surgery using a small size glaucoma implant has the advantage in that the surgery can be completed if only a small size glaucoma implant is inserted into the anterior chamber of the eye under the conjunctiva. However, in order to discharge aqueous humor from the eye at the appropriate pressure, the dimensions, such as diameter, length, etc., of respective parts of the glaucoma implant having a very small size need to be precisely adjusted, and if the dimensions are not carefully designed, the aqueous humor may be excessively discharged, causing the low intraocular pressure, or may not be fully discharged. Nevertheless, the design of glaucoma implant tools optimized for the formation pressure in the anterior chamber has not been fully studied yet.

DISCLOSURE

Technical Problem

The present disclosure is intended to improve the problems as described above, and an objective of the present disclosure is to provide an eye disease implant device in which the optimal formation pressure in an anterior chamber of an eye is achieved by an appropriate combination of a tube and a wick inserted into the tube when lowering intraocular pressure by discharging aqueous humor through the tube inserted into the eye, and the tube and an implant body are able to be coupled to or decoupled from each other according to need or circumstances.

Technical Solution

In an embodiment of the present disclosure, an eye disease implant device for adjusting intraocular pressure includes a tube body having one end inserted into an anterior chamber of an eye and the other end inserted into a conjunctival tissue or a tenon tissue of the eye, the tube body including a hollow channel and being configured to discharge aqueous humor, produced in the anterior chamber of the eye, to the conjunctival tissue or tenon tissue via the hollow channel; and a wick configured to be inserted into the hollow channel of the tube body to adjust the formation pressure in the anterior chamber through the tube body.

In an embodiment, the length of the tube body, the diameter of the hollow channel, and the diameter of the wick may be determined such that the formation pressure in the anterior chamber through the tube body amounts to 4 to 14 mmHg.

In an embodiment, the length of the tube body may be 4 to 10 mm, the diameter of the hollow channel may be 0.002 to 0.009 inches, and the diameter of the wick may be 20 to 180 μm.

In an embodiment, the implant device may further include an implant body into which one end of the tube body is detachably inserted and having an aqueous humor-accommodating space therein.

In an embodiment, the implant body may include a lower plate and an upper plate oppositely coupled to each other with the accommodating space defined therebetween, the implant body having a curvature corresponding to that of the eye.

In an embodiment, the lower plate or the upper plate may include an inlet through which the tube body is inserted into the accommodating space; and one or more outlets through which the aqueous humor is discharged from the accommodating space out of the implant body.

In an embodiment, one or more of the lower plate or the upper plate may further include one or more fastening members composed of or coated with a water-soluble adhesive to detachably couple the lower plate and the upper plate to each other.

In an embodiment, one or more of the lower plate and the upper plate may be composed of polyurethane. In addition, in an embodiment, the thickness of the lower plate or the upper plate may be 0.2 to 0.5 mm.

In an embodiment, the tube body may be composed of polytetrafluoroethylene, a urethane-based material including polycarbonate polyurethane, a silicone-based material including polydimethylsiloxane (PDMS), or siloxane-based polyurethane.

Advantageous Effects

According to the embodiments of the eye disease implant device, the inner diameter of the tube, the diameter of the wick inserted into the tube, and the like are designed such that the optimal formation pressure in the anterior chamber is achieved when lowering intraocular pressure by discharging aqueous humor to the conjunctiva tissue or tenon tissue through the tube inserted into the anterior chamber of the eye, thereby solving the problem of insufficient discharge of the aqueous humor or the low intraocular pressure due to excessive discharge of the aqueous humor.

In addition, the implant device according to the embodiment of the present disclosure is configured to allow the tube and the implant body to be coupled or decoupled according to the need or circumstances, and is designed to have a structure for minimizing the eye damage and attendant complications due to the tube or implant body disposed or inserted into the eye, thereby minimizing the damage of the corneal endothelium and attendant side effects such as corneal endothelium loss due to the implant device.

MODE FOR INVENTION

Figure 1:
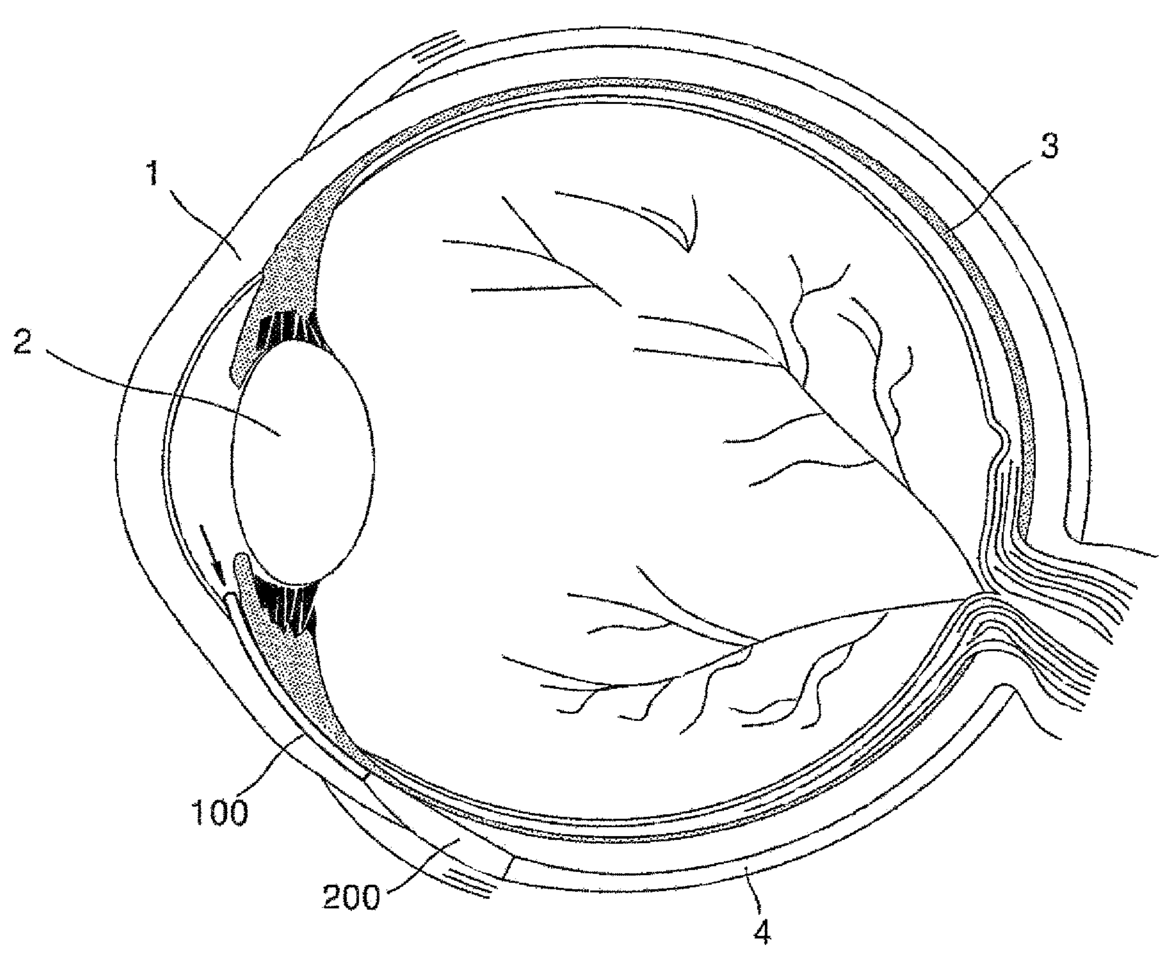
FIG. 1 is a conceptual diagram illustrating an eye disease implant device inserted into the eye according to an embodiment.

The terms used herein will be briefly described, and then the present disclosure will be described in detail.

Although currently widely used general terms have been selected and used herein, considering the function in the present disclosure, this may vary depending on the intention or practice of a skilled person in the art, the emergence of new technologies, or the like. In addition, in certain cases, there are some terms selected by the applicant, and in this case, the meanings thereof will be described in detail in the corresponding description of the present disclosure. Therefore, the terms used herein should be defined based on the meanings of the terms and throughout the content of the present disclosure, not just on the names of the terms.

When a part "includes" a component as described in the entire specification, it means that the part may further include other components without excluding other components unless otherwise stated. In addition, when a part is "connected" with other part as described in the specification, it means that the part is "connected directly" with other part, or connected with other part "with a further part interposed therebetween".

Hereinbelow, embodiments of the present disclosure will be described in detail so that the embodiments can be easily implemented by a person having ordinary skill in the art to which the present disclosure pertains. However, the present disclosure is not limited to the disclosed embodiments, but may be implemented into various different forms. In addition, in order to clearly describe the present disclosure in the drawings, elements that are not relevant to the corresponding description were omitted, and like elements are denoted as like reference numbers throughout the specification.

The present disclosure will be described in detail with reference to the accompanying drawings.

FIG. 1 is a conceptual diagram illustrating an eye disease implant device inserted into the eye according to an embodiment.

Referring to FIG. 1, the eye disease implant device according to the embodiment of the present disclosure is to control a discharge amount of aqueous humor produced in an anterior chamber located in front of the lens 2 in the eye 1 to adjust intraocular pressure, which makes it possible to prevent the optic nerve from being damaged due to increased intraocular pressure by eye diseases. The eye disease implant device according to the embodiment of the present disclosure may be used to treat various eye diseases causing or caused by an increase in intraocular pressure or relieve symptoms generated by the eye diseases.

The eye diseases stated in the present specification may include glaucoma caused by increased intraocular pressure, and the glaucoma may include, but is not limited thereto, congenital glaucoma, traumatic glaucoma, glaucoma suspect, high tension glaucoma, primary open angle glaucoma, normal tension glaucoma, capsular glaucoma with pseudoexfoliation of lens, chronic simple glaucoma, low tension glaucoma, pigmentary glaucoma, primary angle closure glaucoma, acute angle closure glaucoma, chronic angle closure glaucoma, intermittent angle closure glaucoma, glaucoma associated with ocular trauma, glaucoma associated with ocular inflammation, drug-induced glaucoma, neovascular glaucoma, uveitic glaucoma, or the like.

The eye disease implant device may be configured in the form of a tube 100, which is applicable to a micro-invasive glaucoma surgery (MIGS), wherein one end of the tube 100 is inserted into an anterior chamber of the eye 1 and the other end of the tube is inserted into a conjunctiva tissue or tenon tissue 4. The eye disease implant device may be inserted and disposed into the conjunctiva tissue or tenon tissue 4 of the eye 1 by peeling the conjunctiva tissue or tenon tissue 4, inserting the implant device into the conjunctiva tissue or tenon tissue, and covering the implant device with the conjunctiva tissue or tenon tissue by the operation of a surgeon. Alternatively, the eye disease implant device may be placed in the eye as illustrated in FIG. 1 by being injected into the eye through an injector so that the implant device is partially inserted into the anterior chamber of the eye. Here, the injector refers to a device that injects the implant device into the eye by mechanically pushing the implant device accommodated therein.

In the eye disease implant device, the implant body 200 may be further coupled to the other end of the tube 100 to be inserted into the conjunctiva tissue or tenon tissue 4 of the eye 1. The implant body 200 is coupled onto the rear side of the tube 100 so as to temporarily accommodate the aqueous humor for effective control of intraocular pressure. After the tube 100 of the eye disease implant device is partially inserted into the anterior chamber of the eye 1, the implant body 200 may be coupled to and disposed on the rear side of the tube through the peeled conjunctiva tissue or tenon tissue in consideration of the clinical circumstances such as a patient's status change, a fibrosing rate, or the like.

Alternatively, in some embodiments, the tube 100 and the implant body 200 may also be placed together in the eye 1 through the peeled conjunctiva tissue or tenon tissue 4 of the eye in a combined state or an integrated state. That is, depending on the clinical needs or situations, the implant body may be pre-coupled to the tube 100 before the implant device is placed in the eye 1, or the implant body 200 may be combined with the tube 100 that has been first placed in the eye.

When the eye disease implant device is inserted into the eye 1, the aqueous humor produced from the anterior chamber flows through and is discharged out of the tube 100 of the implant device, thereby lowering intraocular pressure. If the implant body 200 is coupled to the tube, the aqueous humor discharged from the anterior chamber may be temporarily accommodated in the implant body 200. If the amount of the aqueous humor accommodated in the implant body exceeds a threshold value, the accommodated aqueous humor may be discharged to the conjunctiva tissue or the tenon tissue 4 through the rear side of the implant body 200, thereby effectively adjusting intraocular pressure.

Embodiments of the eye disease implant device will be described in detail with reference to FIGS. 2 to 6.

Figure 2:
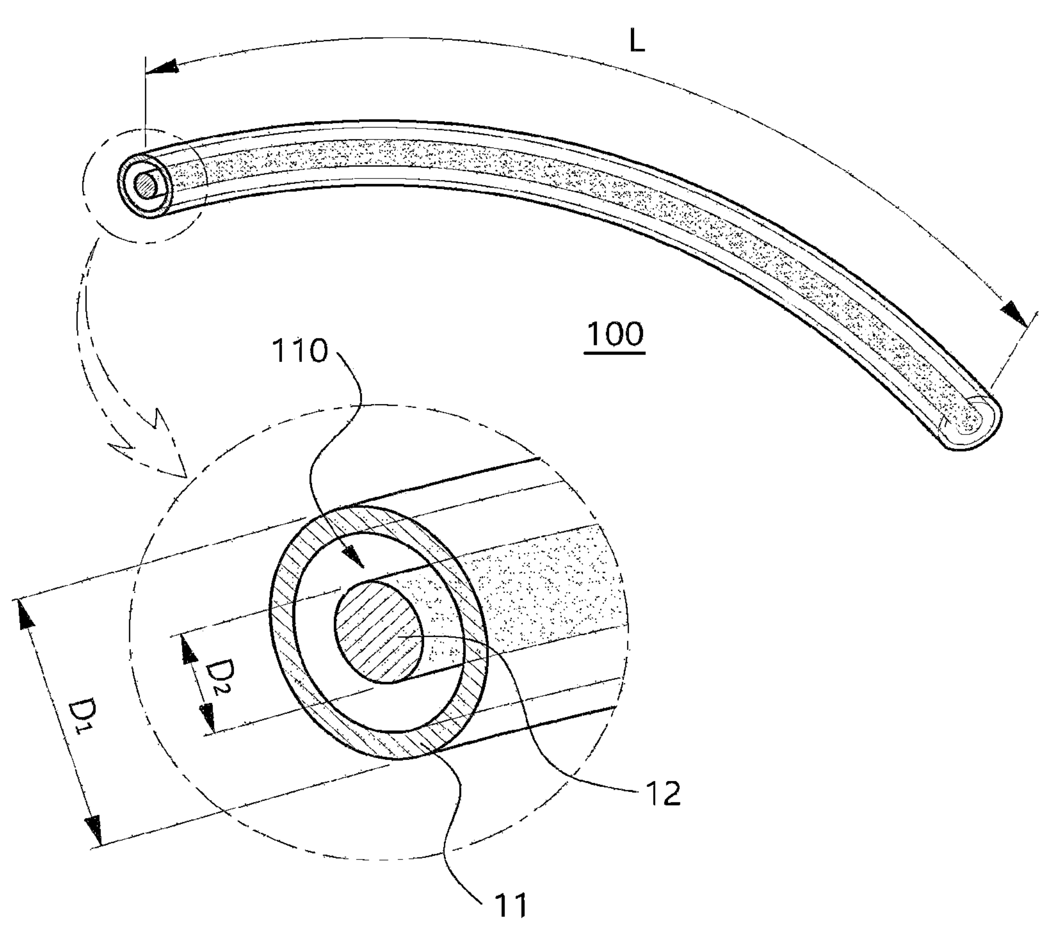
FIG. 2 is a perspective view illustrating an eye disease implant device according to an embodiment.

FIG. 2 is a perspective view illustrating an eye disease implant device according to an embodiment.

Referring to FIG. 2, the eye disease implant device according to the present embodiment has the form of a tube 100 applicable to the MIGS, and the tube 100 includes a tube body 11 having a hollow channel 110, and a wick 12 inserted into the hollow channel 110 of the tube body 11. The tube body 11 may be made of a deformable biocompatible material. The tube configured as described above is inserted into the anterior chamber and the conjunctiva tissue or tenon tissue of the eye at both ends thereof so that the aqueous humor produced from the anterior chamber of the eye can be discharged to the conjunctiva tissue or tenon tissue through the hollow channel 110.

The tube body 11 may be composed of, but not limited thereto, polytetrafluoroethylene (PTFE), a urethane-based material including polycarbonate polyurethane, a silicone-based material including polydimethylsiloxane (PDMS), or siloxane-based polyurethane.

In an embodiment, the tube body 11 may form a curve having a predetermined curvature to prevent damage to the corneal endothelium in the eye. Due to the different sizes of eyeballs and the different tube-injection skills for each patient, the front end of the tube may pierce through and damage the cornea in the anterior chamber of the eye during the insertion of the tube into the anterior chamber of the eye. Such corneal damage may cause complications, such as corneal failure, which may require a corneal transplant later.

According to the present embodiment, the tube body 11 may be bent as illustrated in FIG. 2 to have a predetermined curvature corresponding to the curvature of the eye surface such that the movement of the tube can form a curve naturally in the process of entering the anterior chamber of the eye.

The wick 12 is inserted into the hollow channel 110 at least partially to adjust the formation pressure in the anterior chamber through the hollow channel 110 of the tube body 11. When the wick 12 is inserted into the hollow channel 110 of the tube body 11, a flow of aqueous humor is not smooth and thus is accumulated in the anterior chamber of the eye, so that intraocular pressure increases compared to the case without the wick 12. As used herein, the formation pressure in the anterior chamber means the formation pressure in the anterior chamber formed at this time.

If the wick 12 is thick, the space between an inner wall and the tube body 11 and the wick 12 is narrowed, so the aqueous humor is relatively slowly discharged, and accordingly, the formation pressure in the anterior chamber increases. On the contrary, if the wick 12 is thin, the space between the inner wall of the tube body 11 and the wick 12 is widened, so the aqueous humor is a relatively quickly discharged, and accordingly, the formation pressure in the anterior chamber decreases. Thus, through the appropriate configuration of the wick 12, the formation pressure in the anterior chamber may be optimized to, for example, about 6 to 21 mmHg after surgery. However, the preferred range of the formation pressure in the anterior chamber is not limited thereto.

The wick 12 may be a non-absorbent surgical suture, which may be composed of, but not limited to, nylon or prolene, for example. In the tube 100 of the eye disease implant device according to the embodiments of the present disclosure, the length L of the tube body 11, the dimension of the diameter $D_1$ of the hollow channel 110 formed in the tube body 11 (i.e., the inner diameter of the tube body 11) perpendicular to the longitudinal direction of the tube body 11, and/or the diameter $D_2$ of the wick 12 perpendicular to the longitudinal direction of the tube body 11 may be determined to be a value to optimize the formation pressure in the anterior chamber.

Specifically, the formation pressure in the anterior chamber through the tube body 11 in which the wick 12 is inserted is determined by a flow rate of aqueous humor flowing from the eyeball, and at the same time, is affected by the length L of the tube body 11, the inner diameter $D_1$ of the tube body 11, and the diameter $D_2$ of the wick 12. The present inventors derive the optimal formation pressure in the anterior chamber by changing one or more of the length L of the tube body 11, the inner diameter $D_1$ of the tube body 11, and the diameter $D_2$ of the wick 12 in an environment in which the aqueous humor is introduced at a flow rate similar to an actual flow rate of the aqueous humor from the eyeball.

Table 1 below shows the formation pressure in mmHG unit in the anterior chamber measured while changing the length L of the tube body 11 and the diameter $D_2$ of the wick 12. In the test results shown in Table 1, approximately 0.003 inch-inner diameter $D_1$ tube body 11 was used, and the flow rate of the aqueous humor was fixed to about 2 μL/min.

TABLE 1

| | | Length L of Tube Body 11 (mm) | | | | | |
|---|---|---|---|---|---|---|---|
| | | 4 | 5 | 6 | 7 | 8 | 9 |
| Diameter | 0.041 | 3.4 ± 0.5 | 4.1 ± 0.6 | 5.5 ± 0.4 | 7.9 ± 2.2 | 9.0 ± 2.5 | 8.6 ± 0.8 |
| D2 of | 0.045 | 5.8 ± 1.0 | 7.4 ± 1.1 | 7.6 ± 0.5 | 10.6 ± 1.1 | 10.8 ± 1.0 | 13.2 ± 2.3 |
| Wick 12 | 0.050 | 7.2 ± 1.0 | 8.1 ± 1.8 | 9.6 ± 0.6 | 12.8 ± 1.5 | 13.1 ± 1.1 | 14.8 ± 2.7 |
| (mm) | 0.061 | 32.6 ± 0.9 | 45.4 ± 5.0 | 25.5 ± 3.1 | 54.5 ± 3.9 | 55.1 ± 15.3 | 70.3 ± 2.1 |

In addition, Table 2 below shows the formation pressure in mmHg unit in the anterior chamber measured while changing the inner diameter $D_1$ of the tube body 11 and the diameter $D_2$ of the wick 12, assuming that the length L of the tube body 11 is 6 mm, and the flow rate of the aqueous humor is fixed to about 2 μL/min.

TABLE 2

| | | Inner Diameter D1 of Tube Body 11 (inch) | | |
|---|---|---|---|---|
| | | 0.003 | 0.004 | 0.005 |
| Diameter D2 of | 0.033 | 3.4 ± 0.7 | | |
| Wick 12 | 0.041 | 5.5 ± 0.4 | | |
| (mm) | 0.045 | 7.6 ± 0.5 | | |
| | 0.050 | 9.6 ± 0.6 | 7.8 ± 0.1 | |
| | 0.061 | 32.6 ± 0.9 | 21.7 ± 1.6 | |
| | 0.064 | | 23.8 ± 2.1 | 4.7 ± 0.6 |
| | 0.076 | | | 14.5 ± 2.4 |
| | 0.086 | | | 1.9 ± 0.1 |

It is preferable that the formation pressure in the anterior chamber through the tube of the eye disease implant device according to embodiments has a range of about 4.0 to 14 mmHg through the perfusion test. When applied to the actual patient, the aqueous humor is discharged at the pressure obtained by adding the basic vein pressure of 6 mmHg to the above-mentioned pressure, but the numerical values related to the formation pressure in the anterior chamber are defined as values obtained by subtracting the basic vein pressure to derive the optimal range.

In an embodiment, the length L of the tube body 11, the inner diameter $D_1$ of the tube body 11, and the diameter $D_2$ of the wick 12 are determined such that the formation pressure in the anterior chamber through the tube 100 of the implant device amounts to about 4.0 to 14 mmHg. If the formation pressure in the anterior chamber is less than about 4.0 mmHg, even when the basic vein pressure is added, the pressure is only 10 mmHg, which may cause low intraocular pressure due to excessive discharge of aqueous humor. On the other hand, if the formation pressure in the anterior chamber exceeds about 14 mmHG, when added with the basic vein pressure, the pressure exceeds 20 mmHg, resulting in insufficient discharge of the aqueous humor, which makes it difficult to adjust intraocular pressure.

In an embodiment, the length of the tube body 11 derived to achieve the above optimal range of formation pressure is 4 to 10 mm. In an embodiment, the length of the tube body may be 4 to 9 mm. In addition, in an embodiment, the inner diameter $D_1$ of the tube body 11 derived to achieve the above optimal range of formation pressure is 0.002 to 0.009 inches. In an embodiment, the inner diameter $D_1$ of the tube body 11 may be 0.002 to 0.005 inches. Furthermore, in an embodiment, the diameter $D_2$ of the wick 12 derived to achieve the above optimal range of formation pressure is 20 to 180 μm (i.e., 0.02 to 0.180 mm). In an embodiment, the diameter $D_2$ of the wick 12 may be 20 to 75 μm (i.e., 0.02 to 0.075 mm). In addition, in an embodiment, the diameter $D_2$ of the wick 12 may be 40 to 75 m (i.e., 0.04 to 0.075 mm).

For example, the present inventors derived a numerical range related to one or more combinations of the length L of the tube body 11, the inner diameter $D_1$ of the tube body 11, and the diameter $D_2$ of the wick 12 on the basis of the experimental results as shown in Table 1 and Table 2 and the preferred formation pressure in the anterior chamber.

As shown in Table 1, in a state in which the flow rate of the aqueous humor and the inner diameter $D_1$ of the tube body 11 are fixed, the formation pressure in the anterior chamber is affected by the length L of the tube body 11 and the diameter $D_2$ of the wick 12, which may be determined such that a pre-set formation pressure in the anterior chamber is achieved.

As shown in Table 1, it was confirmed that when the wick 12 having the diameter $D_2$ of about 0.041 mm is used, the length of the tube body 11 preferably amounts to 5 to 9 mm; when the wick 12 having the diameter $D_2$ of about 0.045 mm is used, the length of the tube body 11 preferably amounts to 4 to 9 mm; and when the wick 12 having the diameter $D_2$ of about 0.050 mm is used, the length of the tube body 11 preferably amounts to 4 to 8 mm.

On the other hand, it was confirmed that when the diameter $D_2$ of the wick 12 is 0.061 mm, the formation pressure in the anterior chamber is too high regardless of the length of the tube body 11, and when the diameter $D_2$ of the wick 12 is less than 0.04 mm, the formation pressure in the anterior chamber is too low. Therefore, in one embodiment, the diameter $D_2$ of the wick 12 may amount to 0.04 to 0.06 mm, i.e., about 40 to 60 m.

In addition, as shown in Table 2, the flow rate of the inner water and the length L of the tube body 11 is fixed, and the forward forming pressure is the inner formation pressure of the tube body 11 and the wick 12 of the tube body 11 and the wick 12 It is affected by the diameter D2, and the diameter D1 of the tube body 11 and the diameter D2 of the wick 12 may be determined so as to achieve the predetermined forward formation pressure.

As shown in Table 2, it was confirmed that when the inner diameter $D_1$ of the tube body 11 is 0.003 inches (i.e., about 0.076 mm), the diameter $D_2$ of the wick 12 preferably amounts to about 0.041 to 0.050 mm, when the inner diameter $D_1$ of the tube body 11 is 0.004 inches (i.e., about 0.1016 mm), the diameter $D_2$ of the wick 12 preferably amounts to about 0.050 to 0.056 mm, and when the inner diameter $D_1$ of the tube body 12 is 0.005 inches (i.e., about 0.127 mm), the diameter $D_2$ of the wick 12 preferably amounts to about 0.064 to 0.074 mm. If the inner diameter $D_1$ of the tube body 11 is 0.004 inches and the diameter $D_2$ of the wick 12 is about 0.061 mm, and if the inner diameter $D_1$ of the tube body 11 is 0.005 inches and the diameter $D_2$ of the wick 12 is about 0.076 mm, the formation pressure in the anterior chamber amounts to 21.7 mmHg and 14.5 mmHg, respectively, which are out of the optimal range.

However, the numerical values described herein are according to some embodiments of the present disclosure, so the dimensions of the tube body 11 and the wick 12 are not limited thereto, but may vary depending on the embodiments.

In one embodiment, the wick 12 may be modified by a clinician to regulate the formation pressure in the anterior chamber. For example, when the wick 12 is introduced into the hollow channel 110 of the tube body 11 and exposed to the outside through the rear end of the tube body 11, the clinician can modify the wick 12 to adjust the discharge amount of the aqueous humor. That is, the clinician can use the wick 12 to properly adjust intraocular pressure according to the patient's condition. In the present embodiment, in order to prevent the user from feeling a foreign body due to the wick 12 exposed to the outside of the tube body 11, the wick 12 may be configured such that the diameter thereof gradually decreases from a point at which the wick is exposed from the tube body 11 or the implant body 200.

In addition, in one embodiment, a marker (not shown) or a protrusion may be formed in a region of an outer surface of the tube body 11. Since one end of the tube body 11 is located in the anterior chamber 1 of the eye and the other end is located in the conjunctiva tissue or tenon tissue in order to discharge the aqueous humor, the entire tube body 11 should not be completely introduced into the anterior chamber 1 of the eye.

Therefore, in one region of the outer surface of the tube body 11, a color marker protrusion (not shown) may be formed to identify the location of the tube body 11 in the eye, so the clinician can easily check that the tube 100 has been introduced enough to effectively discharge the aqueous humor in the surgery process of moving the implant device into the anterior chamber 1 of the eye. Alternatively, a stepped protrusion (not shown) may be formed on one area of the outer surface of the tube body 11 to physically prevent the tube 100 from being excessively inserted into the eye and to prevent or minimize the inserted tube 100 from moving back and forth due to the stepped structure.

Figure 3:
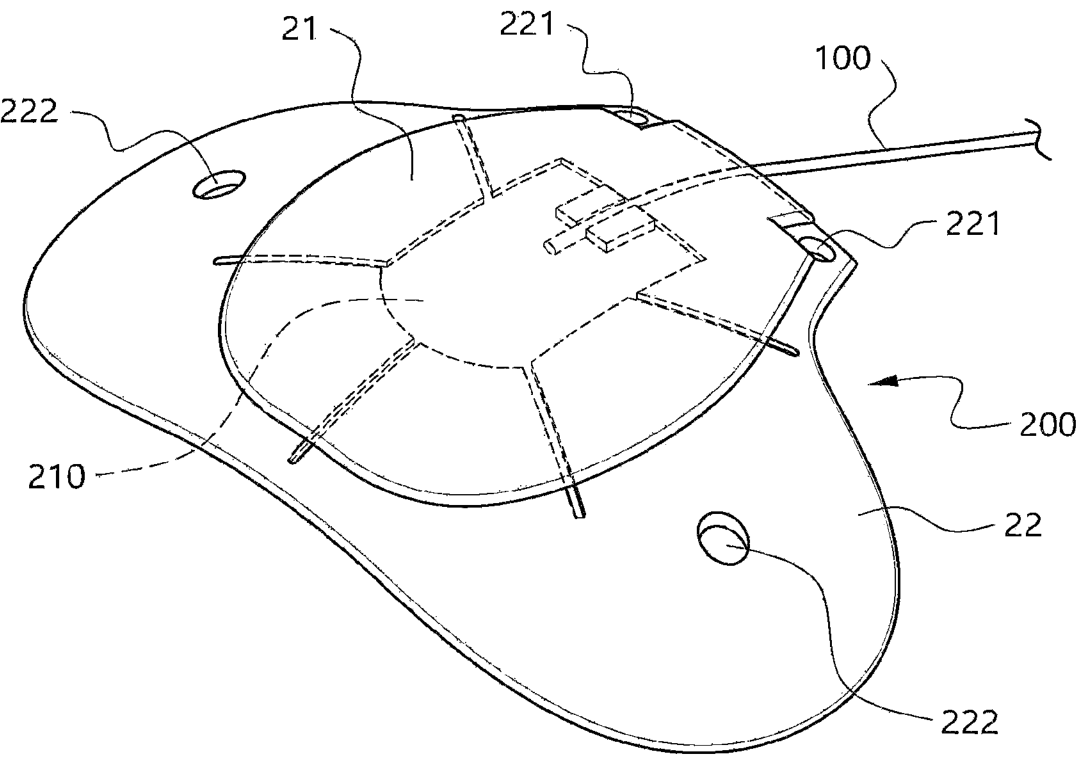
FIG. 3 is a perspective view illustrating the eye disease implant device having an implant body according to the embodiment.

FIG. 3 is a perspective view illustrating the eye disease implant device having an implant body according to the embodiment.

Referring to FIG. 3, the eye disease implant device according to the present embodiment may further include an implant body 200 into which one end of the tube 100 is inserted and having an accommodating space 210 therein. Although not illustrated in the drawing, the tube 100 includes a wick inserted into the tube body as described above with reference to FIG. 2.

The implant body 200 may be detachably coupled to the tube 100, and serves to prevent the exposure and decoupling of the tube 100, and at the same time, to temporarily accommodate aqueous humor. In addition, the implant body 200 may also prevent the hollow channel of the tube 100 from being blocked as the biological tissue grows over the rear end of the tube 100 by blocking the rear end of the tube 100 in the long term. That is, by combining the implant body 200 with one region of the rear side of the tube 100, it is possible to minimize the side effects that the body tissue blocks the rear end of the tube 100 over the time so that intraocular pressure is raised again.

In one embodiment, the implant body 200 includes an upper plate 21 and a lower plate 22 oppositely coupled to each other, and an aqueous humor-accommodating space 210, into which a portion of the rear side of the tube 100 is inserted, may be formed between the coupled upper plate 21 and lower plate 22. Since the upper plate 21 and the lower plate 22 can be coupled to or decoupled from each other, the tube 100 and the implant body 200 may be easily coupled or decoupled through the coupling of the upper plate 21 and the lower plate 22. The specific coupling form of the tube 100 and the implant body 200 will be described later in detail with reference to FIG. 6.

Figure 4A:
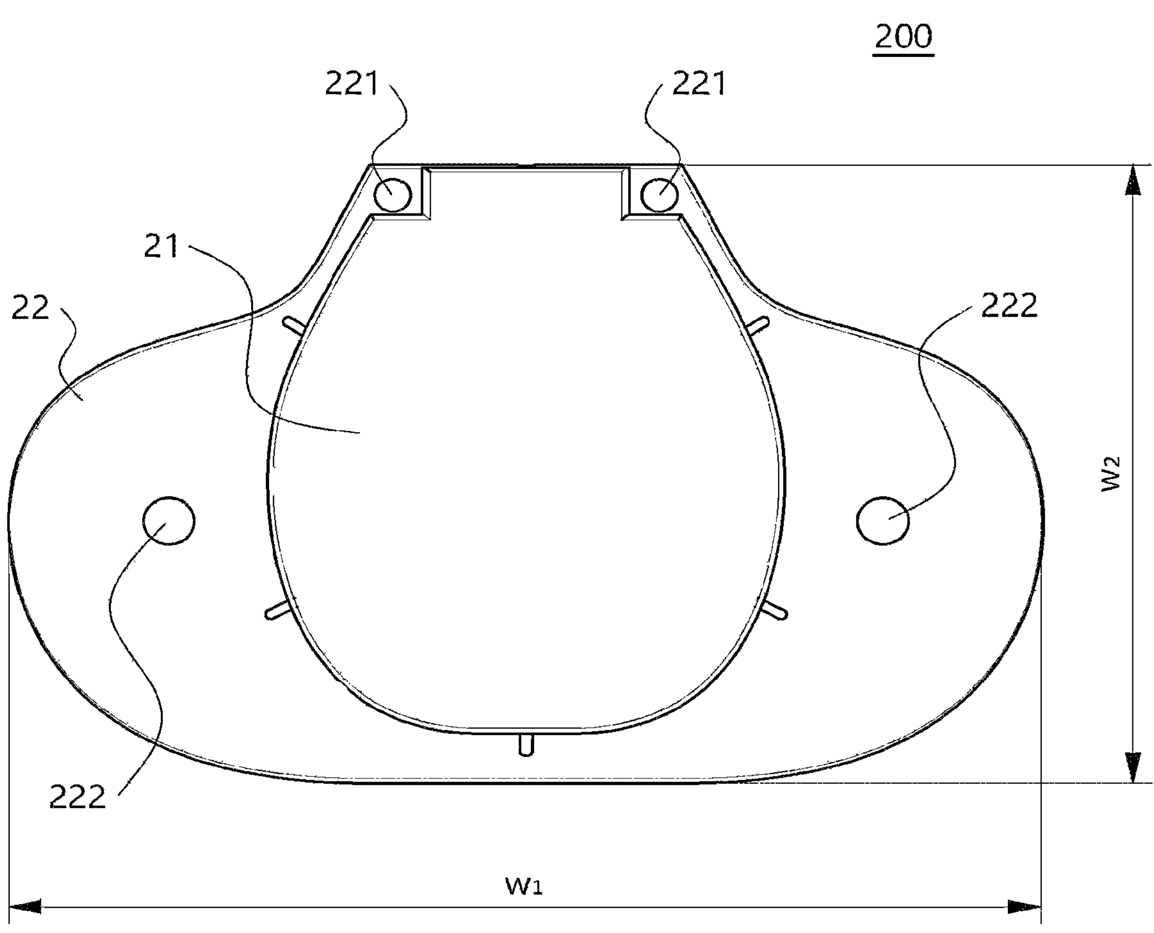
FIG. 4*a* is a plan view illustrating the implant body of the eye disease implant device according to the embodiment.
Figure 4B:
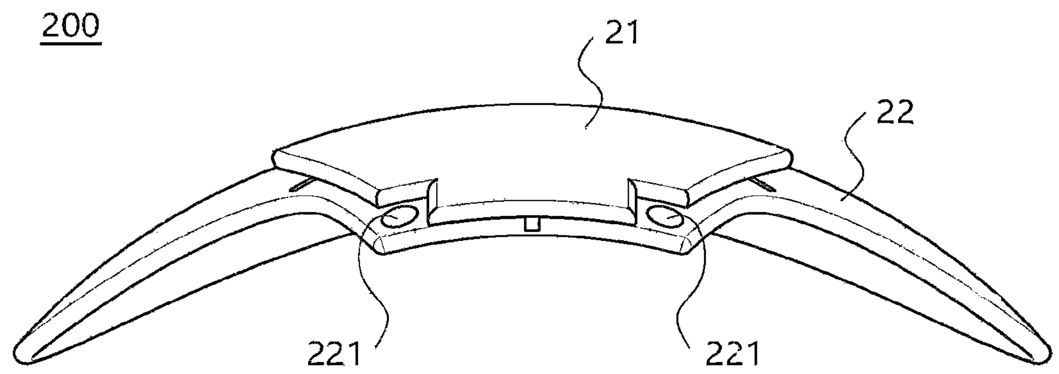
FIG. 4*b* is a front view illustrating the implant body illustrated in FIG. 4*a*.
Figure 4C:
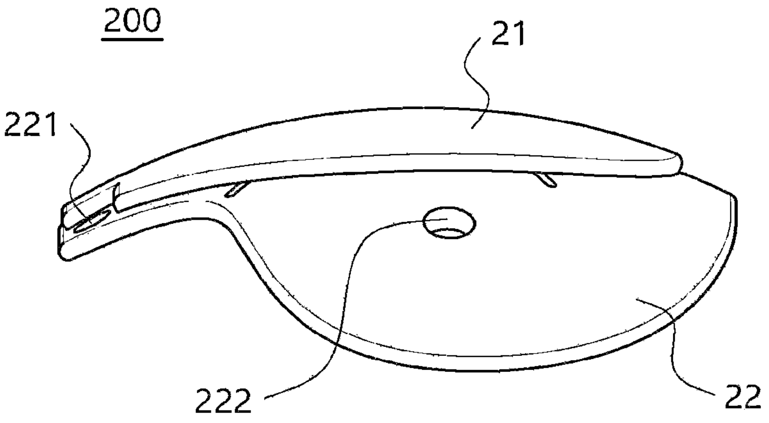
FIG. 4*c* is a side view illustrating the implant body illustrated in FIG. 4*a*.

FIG. **4*a* is a plan view illustrating the implant body of the eye disease implant device according to the embodiment, FIG. 4*b* is a front view illustrating the implant body illustrated in FIG. 4*a*, and FIG. 4*c* is a side view illustrating the implant body illustrated in FIG. 4*a***.

Referring to FIGS. **4*a* to 4*c*, the implant body 200 of the eye disease implant device according to the present embodiment may include a lower plate 22 having streamlined wings located on both sides about the aqueous humor-accommodating space 210, and an upper plate 21 that is oppositely coupled to the lower plate 22 to cover a portion of the lower plate 22, particularly, the region over the aqueous humor-accommodating space 210**.

The upper plate 21 and the lower plate 22 may prevent the cell tissue from penetrating into and blocking the tube by covering one end of the tube inserted into the implant body 200 with the upper plate 21 so that the corresponding one end of the tube is disposed between the upper plate 21 and the lower plate 22. In addition, between the upper plate 21 and the lower plate 22, in addition to the aqueous humor-accommodating space 210, an outlet path is formed so that when the aqueous humor is collected in the accommodating space 210, the aqueous humor can be discharged to the peripheral portion of the implant body 200 therethrough. To this end, one or more discharge openings 221 and 222 may be formed in areas of the lower plate 22 that are not covered by the upper plate 21 in order to discharge the aqueous humor from the implant body 200 to the peripheral tissue therethrough.

In addition, the upper plate 21 and the lower plate 22 may be formed in a sufficiently thin thickness so that the implant body 200 is prevented from being thickened so as not to cause the surgical side effects. Accordingly, the upper plate and the lower plate may be formed of a polyurethane material such as polycarbonate, carbothane, etc., which can be molded in a thin thickness. In the case of polyurethane-based materials, it is possible to form an implant body 200 that has a thin thickness, excellent mechanical properties such as workability, flexibility, and strength, excellent chemical resistance, along with biocompatibility, and excellent oxidative stability. In addition, the implant body 200 formed of such materials provides an advantage in that the implant body is configured to be colored or in-body softened.

On the other hand, in one embodiment, the upper plate 21 and the lower plate 22 may be formed of silicone-based materials such as PTFE and PDMS, or a compound of silicon-based materials such as PDMS-PU and polyurethane-based materials to avoid problems such as biodegradation or the like.

In one embodiment, each of the upper plate 21 and the lower plate 22 may have a thickness of 0.2 to 0.5 mm. For example, in one embodiment, the thickness of the upper plate 21 may be 0.3 mm, and the thickness of the lower plate 22 may be 0.4 mm. In addition, in one embodiment, the width $W_1$ of the lower plate 22 measured in a direction orthogonal to the insertion direction of the tube, including both wings, may be about 18 to 22 mm. In addition, in one embodiment, the width $W_2$ of the lower plate 22 measured in the longitudinal direction of the tube may be about 11 to 15 mm.

However, the above-described numerical values are exemplary, and the shape and size of respective parts of the implant body of the implant device according to the embodiments are not limited to the above-described numerical values.

On the other hand, in one embodiment, as illustrated in the drawings, the edges of the upper plate 21 and/or lower plate 22 may be formed in a streamlined shape that is not angled or sharpened in order to prevent the biological tissue of the eye from being damaged by the upper plate 21 or the lower plate 22. In addition, the upper plate 21 and the lower plate 22 of the implant body 200 have a bent surface to have a predetermined curvature so that the upper plate and the lower plate are arranged in the eye such that the bent portions abut against the curved contour of the eye. For example, the curvature of the upper plate 21 and the lower plate 22 may be determined to correspond to the case of the eye having an average diameter of 25 mm, but the present disclosure is not limited thereto.

Figure 5:
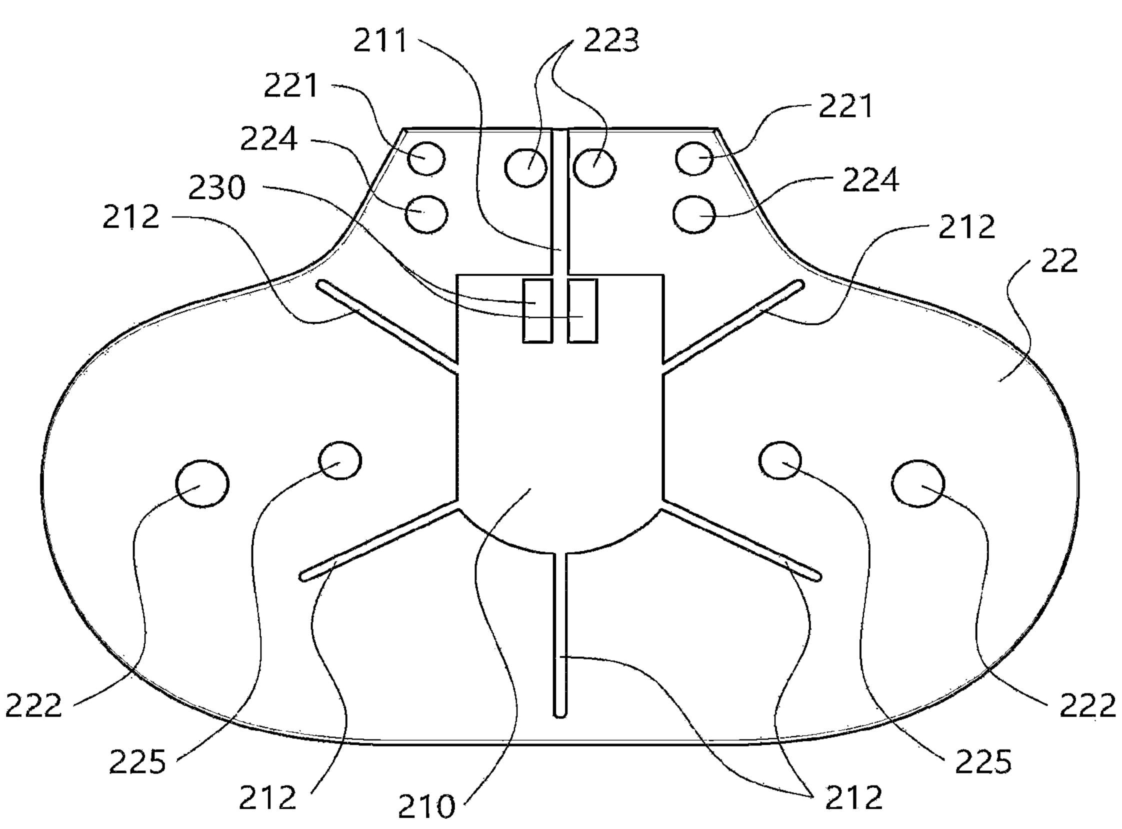
FIG. 5 is a plan view illustrating a lower plate of the implant body of the eye disease implant device according to the embodiment.
Figure 6:
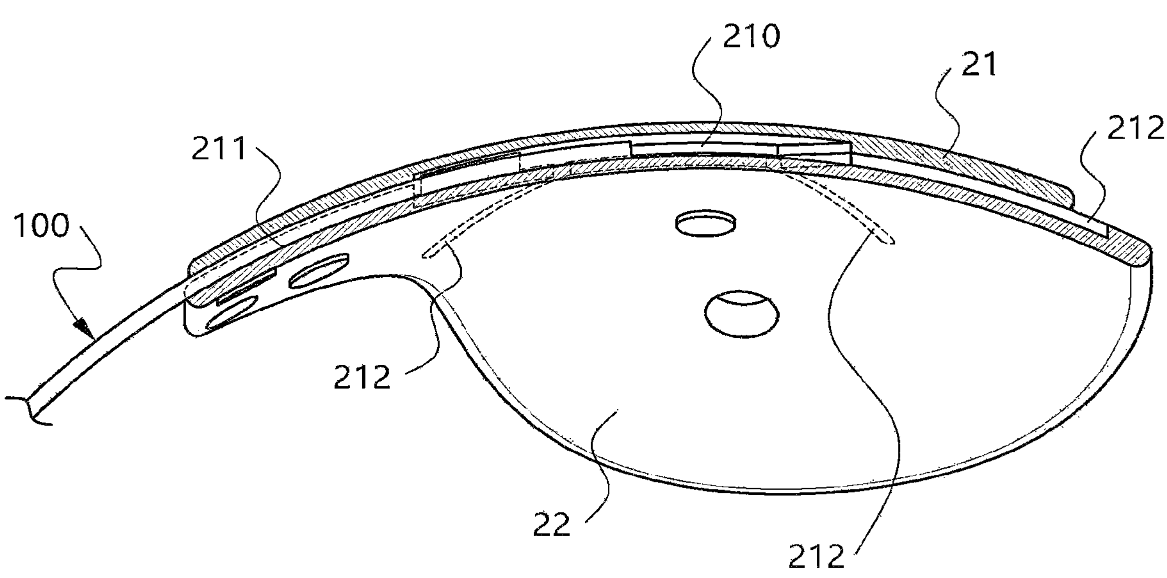
FIG. 6 is a cross-sectional view illustrating the eye disease implant device in which the tube is inserted into the implant body according to an embodiment.

FIG. 5 is a plan view illustrating a lower plate of the implant body of the eye disease implant device according to the embodiment, and FIG. 6 is a cross-sectional view illustrating the eye disease implant device in which the tube is inserted into the implant body according to an embodiment.

Referring to FIGS. 5 and 6, the lower plate 22 of the implant body 200 includes an aqueous humor-accommodating space 210 formed in the form of a recessed region in the lower plate 22. The aqueous humor-accommodating space 210 may be defined by the recessed regions formed in both the upper plate 21 and lower plate 22, or by the recessed region formed in either the upper plate 21 or the lower plate 22. In the embodiment illustrated in FIG. 5, although the aqueous humor-accommodating space inner 210 has a modified rectangular shape having four sides of which one side provided at the rear side with respect to the discharge direction of the aqueous humor has a curved shape, this is illustrative, so in other embodiments, the accommodating space may have a circular, oval, or other sectional shape.

In one embodiment, the upper plate 21 and the lower plate 22 may have the same curvature, and the aqueous humor-accommodating space 210 may be defined by recessed region(s) formed in the upper plate 21 and/or lower plate 22. However, in other embodiments, the upper plate 21 may be formed to have a greater curvature compared to the lower plate 22, so that the central part of the upper plate 21 protrudes upwards (i.e., in a direction away from the eye) widely than the central part of the lower plate 22, so that the volume of the aqueous humor-accommodating space 210 is increased as much as the part of the widely protruding upper plate 21.

An inlet path 211, into which the tube is inserted, extends to the edge of the lower plate 22 so as to be connected to the aqueous humor-accommodating space 210. In addition, one or more outlet paths 212 are further connected to the aqueous humor-accommodating space 210 so that the aqueous humor accommodated in the accommodating space 210 can be discharged through the outlet paths. For example, one or more outlet paths 212 may be disposed so as to be connected to remaining sides or apexes of the sectional shape of the aqueous humor-accommodating space 210 other than the side or apex to which the inlet path 211 is connected.

The inlet path 211 and the outlet path 212 are formed, in the lower plate 22, with recessed regions as a waterway through which the aqueous humor may flow. In one embodiment, the width of the outlet path 212 measured in a direction orthogonal to the flow direction of the aqueous humor may be about 0.1 to 0.3 mm. In addition, in one embodiment, the depth of the outlet path 212 may be about 0.1 to 0.3 mm. For example, in one embodiment, five outlet paths each having a width of 0.2 mm and a depth of 0.2 mm may be provided, but the present disclosure is not limited thereto.

In one embodiment, the lower plate 22 may be provided with one or more discharge openings 221 to 225. Some of the discharge openings 221-222 may be located in an area of the lower plate 22 that is not covered with the upper plate 21. In addition, in one embodiment, each outlet path 212 may be formed to extend to the area that is not covered with the upper plate 21 when the lower plate 22 is coupled to the upper plate 21. As a result, even when the upper plate 21 is coupled to the lower plate 22, a portion, for example, an end portion, of the outlet path 212 is not covered with the upper plate 21, so that the aqueous humor accommodated in the accommodating space 210 flows out of the accommodating space 210 through the outlet path 212 and then discharged to the peripheral tissue through the discharge openings 221 and 222.

In addition, some of discharge openings 223 to 225 may be formed in an area of the lower plate 22 that is covered with the upper plate 21 when the lower plate 21 is coupled to the upper plate 21. These discharge openings 223 to 225 serve to discharge the aqueous humor, which is not discharged through the outlet path 212 and fills the accommodating space between the upper plate 21 and the lower plate 22, to the peripheral tissue therethrough.

In one embodiment, one or more fastening members 230 may be provided to the upper plate 21 and/or lower plate 22 to detachably couple the upper plate 21 and the lower plate 22 to each other. In FIG. 6, although the fastening member 230 is shown as being placed on the lower plate 22, this is illustrative, and in other embodiments, one or more fastening members having the same function may be formed on the upper plate 21 or both the upper plate 21 and the lower plate 22.

Each fastening member 230 may be formed to have a physical structure, such as a convex-concave structure, that generates a fastening force through contact. For example, when the fastening member 230 on the lower plate 22 is formed in the form of a convex portion, a corresponding concave portion is formed on an undersurface of the upper plate 21 (i.e., the surface facing the lower plate 22). Accordingly, the upper plate 21 and the lower plate 22 may be detachably coupled to each other by inserting the fastening member 230 on the lower plate 22 into the concave portion on the undersurface of the upper plate 21.

In one embodiment, instead of or in addition to the above convex-concave structure, the fastening member 230 may be composed of or coated with a water-soluble adhesive that generates and increases an adhesion force upon contact with water. In this case, the adhesion force between the upper plate 21 and the lower plate 22 may be increased by the aqueous humor discharged from the anterior chamber of the eye and fed through the tube 100.

However, the shape of the implant body 200 according to the embodiments described with reference to the FIGS. 3 to 6 is illustrative, so the size and shape of the implant body 200 coupled to the tube 100 may be modified according to clinical situations. For example, in some cases, the implant body 200 may be configured such that the end portion of the sclera-side tube is covered only with the upper plate 21 without the lower plate 22 for the ease of surgery. In this case, a medical adhesive or a suture may be used on the upper plate 21 so as to fix the upper plate 21 to the sclera.

The foregoing embodiments of the present disclosure are illustrative, and a person having ordinary skill in the art to which the present disclosure pertains will appreciate that the embodiments are easily modifiable into other specified forms without departing from the technical ideas or essential characteristics of the present disclosure. Therefore, the embodiments described above should be understood as being illustrative in all aspects and not limiting. For example, respective components described as a combined form may be implemented in a discrete form, and similarly, the components described as a discrete form may also be implemented in a combined form.

The scope of the present disclosure is defined by the following claims than the detailed description, and should be construed as containing all changes or modifications derived from the meaning, scope, and equivalent of the claims.

INDUSTRIAL APPLICABILITY

Examples are directed to an eye disease implant device and, more particularly, to an eye disease implant device in which the optimal formation pressure in an anterior chamber of an eye is achieved by an appropriate combination of a tube and a wick inserted into the tube when lowering intraocular pressure by discharging aqueous humor through the tube inserted into the eye, and the tube and an implant body are able to be coupled to or decoupled from each other according to need or circumstances.

The invention claimed is:

1. An eye disease implant device for adjusting intraocular pressure, the device comprising:

a tube body configured to have one end inserted into an anterior chamber of an eye and the other end inserted into a conjunctival tissue or a tenon tissue of the eye, the tube body including a hollow channel and being configured to discharge aqueous humor, produced in the anterior chamber of the eye, to the conjunctival tissue or tenon tissue via the hollow channel; and a wick configured to be inserted into the hollow channel of the tube body to adjust the formation pressure in the anterior chamber through the tube body, wherein the length of the tube body, the diameter of the hollow channel, and the diameter of the wick are determined such that the formation pressure in the anterior chamber through the tube body amounts to 4 to 14 mmHg, and wherein the length of the tube body amounts to 4 to 9 mm, the diameter of the hollow channel amounts to 0.003 to 0.0055 inches, and the diameter of the wick amounts to 41 to 74 μm.

2. The eye disease implant device of claim 1, further comprising an implant body into which one end of the tube body is detachably inserted and having an aqueous humor-accommodating space therein.

3. The eye disease implant device of claim 2, wherein the implant body comprises a lower plate and an upper plate oppositely coupled to each other with the accommodating space defined therebetween, the implant body having a curvature corresponding to that of the eye.

4. The eye disease implant device of claim 3, wherein the lower plate or the upper plate comprises:

an inlet path through which the tube body is inserted into the accommodating space; and one or more outlet paths through which the aqueous humor is discharged from the accommodating space out of the implant body.

5. The eye disease implant device of claim 3, wherein one or more of the lower plate or the upper plate further comprise one or more fastening members composed of or coated with a water-soluble adhesive to detachably couple the lower plate and the upper plate to each other.

6. The eye disease implant device of claim 3, wherein one or more of the lower plate and the upper plate comprises polyurethane, and the thickness of the lower plate or the upper plate amounts to 0.2 to 0.5 mm.

7. The eye disease implant device of claim 1, wherein the tube body comprises polytetrafluoroethylene, a urethane-based material including polycarbonate polyurethane, a silicone-based material including polydimethylsiloxane (PDMS), or siloxane-based polyurethane.

8. The eye disease implant device of claim 1, wherein, the length of the tube body amounts to 4 to 9 mm, the diameter of the hollow channel amounts to 0.003 inches, and the diameter of the wick amounts to 41 to 50 μm.

9. The eye disease implant device of claim 1, wherein, the length of the tube body amounts to 6 mm, the diameter of the hollow channel amounts to 0.003 to 0.004 inches, and the diameter of the wick amounts to 41 to 50 μm.

10. The eye disease implant device of claim 1, wherein, the length of the tube body amounts to 6 mm, the diameter of the hollow channel amounts to 0.0045 to 0.0055 inches, and the diameter of the wick amounts to 62 to 74 μm.

* * * * *